(12) United States Patent
Deisseroth

(10) Patent No.: US 10,149,899 B1
(45) Date of Patent: Dec. 11, 2018

(54) COMPOSITION AND METHOD AGAINST C-DIFFICILE

(71) Applicant: Albert B. Deisseroth, Potomac, MD (US)

(72) Inventor: Albert B. Deisseroth, Potomac, MD (US)

(73) Assignee: MicroVAX, LLC, Warrenton, VA (US)

( * ) Notice: Subject to any disclaimer, the term of this patent is extended or adjusted under 35 U.S.C. 154(b) by 0 days.

(21) Appl. No.: 15/375,455

(22) Filed: Dec. 12, 2016

Related U.S. Application Data

(60) Provisional application No. 62/266,146, filed on Dec. 11, 2015.

(51) Int. Cl.
| | | |
|---|---|---|
| *A61K 39/08* | (2006.01) | |
| *C12N 9/10* | (2006.01) | |
| *C07K 14/705* | (2006.01) | |
| *A61K 39/00* | (2006.01) | |

(52) U.S. Cl.
CPC ........ *A61K 39/08* (2013.01); *C07K 14/70575* (2013.01); *C12N 9/1051* (2013.01); *A61K 2039/575* (2013.01); *C07K 2319/40* (2013.01)

(58) Field of Classification Search
None
See application file for complete search history.

(56) References Cited

U.S. PATENT DOCUMENTS

| | | |
|---|---|---|
| 8,119,117 B2 | 2/2012 | Deisseroth et al. |
| 8,299,229 B2 | 10/2012 | Tang et al. |
| 8,828,957 B2 | 9/2014 | Deisseroth et al. |
| 9,533,036 B2 | 1/2017 | Tang et al. |

OTHER PUBLICATIONS

Voth et al. Clinical Microbiology Reviews, Apr. 2005, 18(2): 247-263.*
S M Frey et al., Localization of two epitopes recognized by monoclonal antibody PCG-4 on Clostridium difficile toxin A., Infection and Immunity, vol. 60, No. 6, p. 2488-2492, 1992, Jun. 1992.
Gregory J Babcock et al., Human Monoclonal Antibodies Directed against Toxins A and B Prevent Clostridium difficile-Induced Mortality in Hamsters, Infection and Immunity, vol. 74, No. 11, p. 6339-6347, Nov. 2006.
Sarah Hemmasi et al., Interaction of the Clostridium difficile Binary Toxin CDT and its Host Cell Receptor LSR, The American Society for Biochemistry and Molecular Biology Inc., JBC Papers in Press Manuscript M115.650523, Apr. 2015.
Jason G. S. Ho et al., Crystal structure of receptor-binding C-terminal repeats from Clostridium difficile toxin A, PNAS vol. 102, No. 51, p. 18373-18378, 2005.
Peter Orth et al., Mechanism of Action and Epitopes of Clostridium difficile Toxin B-neutralizing Antibody Bezlotoxumab Revealed by X-Ray Crystallography, Journal of Biological Chemistry vol. 289, No. 26, p. 18008-18021, Jun. 2014.

* cited by examiner

*Primary Examiner* — Oluwatosin A Ogunbiyi
(74) *Attorney, Agent, or Firm* — Jacob Frank; Glenn Snyder

(57) ABSTRACT

This two-step method used in the *Clostridium difficile* toxin transport is a unique method of delivery. The use of a vaccine (TAA/ecdCD40L) for the interdiction of this two-step delivery toxin system to reduce cell death and the death of human subjects is believed to be unique in the area of neutralizing antibodies for protection against the lethal effects of an infectious agent. The proposed composition/vaccine strategy for *C difficile* is to combine and administer at the same time the two compositions/vaccines for Toxin A, the one composition/vaccine for Toxin B and the one vaccine for CDTb to determine the effect of mixing these compositions/vaccines on protecting mice from a lethal dose of *C difficile*. This is believed to be the first time that two different tandem repeats from the contact of a ligand with its cellular receptor have been used to prevent binding of the ligand to its cellular receptor.

6 Claims, No Drawings

Specification includes a Sequence Listing.

COMPOSITION AND METHOD AGAINST C-DIFFICILE

CROSS-REFERENCE TO RELATED APPLICATIONS

This application claims priority and the benefit under 35 U.S.C. § 119(e) of U.S. Provisional Patent Application No. 62/266,146, filed on Dec. 11, 2015, the disclosure of which is hereby incorporated by reference herein in its entirety.

FIELD OF THE INVENTION

The present invention relates generally to the field of bacterial infections. More specifically, it is directed to novel compositions and methods against the *Clostridium difficile* infection.

BACKGROUND OF THE INVENTION

The following discussion of the background of the invention is merely provided to aid the reader in understanding the invention and is not admitted to describe or constitute prior art to the present invention.

*Clostridium difficile* (*C difficile*) is a gram-positive bacterium that causes 250,000 cases of infection (severe diarrhea, pseudomembranous colitis, colonic rupture, sepsis and death) per year in the USA (1-6) which generates thousands of deaths and costs the health care system over 1 billion dollars per year (2, 6). *C difficile* infects patients in whom, the use of broad spectrum antibiotics has disrupted the normal gut flora.

The bacterium forms spores that makes it persist in all hospital environments (2). *C difficile* is not only resistant to the broad spectrum of antibiotics which destroy normal gut flora, but has become resistant to vancomycin and metronidozole which have been used in the past to treat *C difficile* infections. The infection responds initially to these antibiotics but then relapses and despite initial response upon retreatment, recurs again and again (6). A new virulent strain appears to be resistant to multiple antibiotics (2).

Virulence Factors: The infectivity of *C difficile* is due to 2 exotoxins which are secreted by *C difficile*: Toxin A and Toxin B. Toxin A has a molecular weight (MW) of 308,000 kilodaltons (kDa) and 2,710 amino acids (AA). Toxin B has a MW of 279,000 kDa and consists of 2,366 AA (3). There is a third virulence factor: *Clostridium difficile* transferase (CDT) which is present in hypervirulent strains and consists of two factors: CDTa and CDTb genes (4).

Toxin A is responsible for the first step in the disease process, the binding of Toxin A to its cellular receptors on colonic mucosal cells. This binding results in the death of surface mucosal cells in the colon, leading to increased permeability of the colon leading to the bloody watery diarrhea that is characteristic of the disease (3). Toxin A binds to its receptor through a series of repeating units at its carboxyl terminus (3). The disruption of the surface of the colon caused by Toxin A, then opens the door to entry into mucosal epithelial cells in the colon of Toxin B which is much more devastating to these mucosal cells (3) (see discussion in following sections on Toxin B for mechanism of action). Toxin B carries a glucosyltransferase domain (GTD) which kills cells

DETAILED DESCRIPTION OF THE INVENTION

In this specification, although the preferred embodiments have been described in detail, it should be understood that various changes, substitutions and alterations may be made therein without departing from the spirit and scope of the invention. Therefore, the specification is to be regarded in an illustrative rather than a restrictive sense.

The use of the terms "a" and "an" and "the" and similar referents in the context of describing the invention, are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in a suitable order unless otherwise indicated herein or otherwise clearly contradicted by context.

As used herein, the term "antigen" refers broadly to any antigen or portion thereof to which a human, mammal, bird or other animal can generate an immune response. "Antigen" as used herein refers broadly to a molecule that contains at least one antigenic determinant to which the immune response may be directed. The immune response may be cell-mediated, humoral or both.

As used herein, "antigenic determinant" refers to a single antigenic site or epitope on a complex antigenic molecule or particle, a minimal portion of a molecule that interacts with an antibody or T cell receptor. Antigenic determinants may be linear or discontinuous.

"Pharmaceutically acceptable" in the context of the present invention means a pharmaceutical composition that is generally safe, non-toxic and biologically acceptable for veterinary and human pharmaceutical use. Preferred compositions of this invention are intended for humans or animals.

The phrase "an effective amount" in reference to administering the fusion protein or an expression vector encoding that protein, is an amount that results in an increase in the immune response as measured by an increase in T cell activity and/or antibody production.

The fusion protein recited herein may be formulated with an adjuvant to enhance the resulting immune response. As used herein, the term "adjuvant" in the context of the instant invention means a chemical that, when administered with the expression vector or the fusion protein, enhances the immune response. An adjuvant is distinguished from a carrier protein in that the adjuvant is not chemically coupled to the antigen. Adjuvants are well known in the art and include, but not limited to, mineral oil emulsions (U.S. Pat. No. 4,608,251) such as Freund's complete or Freund's incomplete adjuvant (Freund, *Adv. Tuberc. Res.* 7:130 (1956); Calbiochem, San Diego Calif.), aluminum salts, especially aluminum hydroxide or ALHYDROGEL (approved for use in humans by the U.S. Food and Drug Administration), muramyl dipeptide (MDP) and its analogs such as [Thr$^1$]-MDP (Byersand Allison, Vaccine 5:223 (1987)), monophosphoryl lipid A (Johnson et al., *Rev. Infect. Dis.* 9:S512 (198)), and the like.

The term "vector" which contains a transcription unit (aka the "expression vector") as used herein refers to viral and non-viral expression vectors that when administered in vivo can enter target cells and express an encoded protein. Viral vectors suitable for delivery in vivo and expression of an exogenous protein are well known and include adenoviral vectors, adeno-associated viral vectors, retroviral vectors, vaccinia vectors, pox vectors, herpes simplex viral vectors, and the like. Viral vectors are preferably made replication defective in normal cells. For example, see U.S. Pat. Nos. 6,669,942; 6,566,128; 6,794,188; 6,110, 744; 6,133,029. The vector can be administered parenterally, such as intravascularly, intravenously, intra-arterially, intramuscularly, subcutaneously, or the like. Administration can also be orally, nasally, rectally, transdermally or aerosol inhalation. The vectors may be administered as a bolus, or slowly infused. The vector in the instant application is preferably administered subcutaneously.

The term "transcription unit" as it is used herein in connection with an expression vector means a stretch of DNA that is transcribed as a single, continuous mRNA strand by RNA polymerase, and includes the signals for initiation and termination of transcription. For example, in one embodiment, a transcription unit of the invention includes nucleic acid that encodes from 5' to 3' a secretory signal sequence, an influenza antigen and CD40 ligand. The transcription unit is in operable linkage with transcriptional and/or translational expression control elements such as a promoter and optionally any upstream or downstream enhancer element(s). A useful promoter/enhancer is the cytomegalovirus (CMV) immediate-early promoter/enhancer. See U.S. Pat. Nos. 5,849,522 and 6,218,140.

The term "CD40 ligand" (CD40L) as used herein refers to a full length or portion of the molecule known also as CD154 or TNF5. CD40L is a type II membrane polypeptide having a cytoplasmic domain at its N-terminus, a transmembrane region and then an extracellular domain (ecd) at its C-terminus. Unless otherwise indicated the full length CD40L is designated herein as "CD40L," "wtCD40L" or "wtTmCD40L." The nucleotide and amino acid sequence of CD40L from mouse and human is well known in the art and can be found, for example, in U.S. Pat. No. 5,962,406. Also, included within the meaning of CD40 ligand are variations in the sequence including, but not limited to, conservative amino acid changes and the like which do not alter the ability of the ligand to elicit an immune response in conjunction with the fusion protein of the invention.

The term "neutralizing antibody" as used herein refers to antibodies that reduce the virulence, infectivity or pathogenicity of *C difficile* by partial or complete inactivation of one or more *C difficile* virulence factors.

The term "opsonizing antibody" as used herein refers to antibodies that bind to a receptor on *C difficile* and "mark" it for subsequent ingestion and destruction by phagocytes such as macrophages. In this context, an opsonizing antibody attaches to one or more *C difficile* virulence factors and acts as a binding enhancer for phagocytosis by macrophages The term "secretion" in reference to the fusion protein TAA/ecdCD40L, means that the fusion protein includes elements (such as the secretory or signal sequence) that cause secretion of the TAA/ecdCD40L fusion protein to occur, as opposed to an element such as a transmembrane domain of a cell that does not allow secretion to occur.

Some of the abbreviations used herein include: "Ad" (adenoviral); "sig" (signal sequence); "TAA" (target associated antigen); "ET" (epitope target); "ecd" (extracellular domain); and "sc" (subcutaneous).

The inventor's laboratory has developed a TAA/ecdCD40L (target associated antigen/extracellular domain of the CD40L protein) vaccine platform that is specifically designed to overcome the defective response to vaccination in immunosuppressed, debilitated patients who are of advanced chronological age. One of the reasons for the success of this platform is that it supplies a potent immunostimulatory signal (ecdCD40L) that is missing in older people. The presence of the TAA/ecdCD40L activates the DCs, as well as the antigen specific B cells and T cells, increases the potency of the vaccine, and directs the TAA along a Class I as well as a Class II MHC presentation pathway within the DC. This vaccination can be given subcutaneously as a TAA/ecdCD40L protein, as a subcutaneous injection of the Ad-sig-TAA/ecdCD40L vector, as an intramuscular injection of a DNA plasmid expression vector encoding the TAA/ecdCD40L protein, or as a subcutaneous injection of the fusion protein itself.

The term "secretory signal sequence" (aka. "signal sequence," "signal peptide," leader sequence, "or leader peptide") as used herein refers to a short peptide sequence, generally hydrophobic in charter, including about 20 to 30 amino acids which is synthesized at the N-terminus of a polypeptide and directs the polypeptide to the endoplasmic reticulum. The secretory signal sequence is generally cleaved upon translocation of the polypeptide into the endoplasmic reticulum. Eukaryotic secretory signal sequences are preferred for directing secretion of the exogenous gene product of the expression vector. A variety of suitable such sequences are well known in the art and include the secretory signal sequence of human growth hormone, immunoglobulin kappa chain, and the like. In some embodiments the endogenous tumor antigen signal sequence also may be used to direct secretion.

The term "linker" as used employed in this application with respect to the transcription unit of the expression vector refers to one or more amino acid residues between the carboxy terminal end of the antigen and the amino terminal end of CD40 ligand. The composition and length of the linker may be determined in accordance with methods well known in the art and may be tested for efficacy. (See, e.g. Arai et al. *Protein Engineering*, Vol. 4, No. 8, 529-532, August 2001). In certain embodiments of the present invention, the linker is generally from about 3 to about 15 amino acids long, more preferably about 5 to about 10 amino acids long. However, longer or shorter linkers may be used or the linker may be dispensed with entirely. Longer linkers may be up to about 50 amino acids, or up to about 100 amino acids. One example of a linker well-known in the art is a 15 amino acid linker consisting of three repeats of four glycines and a serine (i.e., [Gly$_4$Ser$_3$]).

The TAA/ecdCD40L vaccine can dramatically increase the potency of the immune response in healthy subjects, as well as subjects in whom the function of CD4 helper T cells is defective and thereby circumvent the functional defects in the immune response that are acquired in such individuals, as well as increase the immunogenicity of target antigens. There are several versions of this vaccine: (a) one in which the TAA/ecdCD40L transcription unit is embedded in a replication incompetent adenoviral vector (Ad-sig-TAA/ecdCD40L) which is used as an initial priming injection, followed by two sc injections of the TAA/ecdCD40L protein; (b) one in which the vaccine consists solely of the TAA/ecdCD40L protein, and (c) one in which the transcription unit for the TAA/ecdCD40L protein is inserted into a plasmid DNA expression vector. The TAA is connected through the linker to the aminoterminal end of the extracellular domain (ecd) of the potent immunostimulatory signal CD40 ligand (CD40L).

The attachment of the TAA to the CD40L accomplishes two things: (a) the binding of the TAA/ecdCD40L protein to the CD40 receptor on the dendritic cells (DCs) as well as on the B cells and T cells, activate these cells thereby replacing the CD40L signal which is missing on the plasma membrane of the CD4 helper T cells of older individuals; and (b) once the TAA/ecdCD40L protein is engaged on the CD40 receptor of the DC, the entire TAA/ecdCD40L protein is internalized into the DC in a way that allows the TAA to be processed through the Class I as well as the Class II MHC presentation pathways. The activated TAA loaded DC then migrate to the regional lymph nodes where they can activate and induce expansion of the TAA specific CD8 effector T cells. These antigen specific CD8 effector cells become increased in number in the lymph nodes, egress from the lymph nodes into the peripheral blood. The antigen specific CD8 effector T cells exit the intravascular compartment and enter into the extravascular sites of inflammation or infection. In addition to showing that this vaccine increases the antigen specific CD8 effector T cells in the sites of inflammation, we have shown that the activation and expansion of the B cells by the TAA/ecdCD40L protein increases the levels of the TAA specific antibodies in the serum.

According to the invention, the *C difficile* composition and method were created as follows:

Proposed Composition/Vaccine Against Toxin A: Antibodies to the carboxy-terminus (C-ter) of Toxin A have been shown to protect mice, rats, and hamsters from otherwise lethal doses of the bacterial toxin and of the bacterial cells (1). Frey and Wilkins had shown that the PCG-4 antibody to Toxin A binds to epitopes located with the repeating units at the carboxyl terminal region of Toxin A which binds to cellular receptors (3). These workers identified that this neutralizing antibody blocks in vitro toxicity of Toxin A to cell lines as well as protects animals against the lethal effects of high doses of the bacterial cells or the purified toxin (3). Their results showed that the antibody recognizes epitopes within two fragments/peptides of Toxin A: amino acid residues 2097-2141 (44 AA long) and amino acid residues 2355-2398 (43 AA long).

The amino acid sequence of the fragment 2097-2141 is as follows:

SEQ ID NO. 1
ATGWQTIDGKKYYFNTNTAEAATGWQTIDGKKYYFNTNTAIAST

The amino acid sequence of the fragment from 2355-2398 is as follows:

SEQ ID NO. 2
ATGWQTIDGKKYYFNLNTAEAATGWQTIDGKKYYFNTNTFIAST

These two peptides each comprise of tandem repeats (shown above as underlined) and the two peptides SEQ ID NO. 1 and SEQ ID NO. 2, are identical except for two AA which are in bold in the first and second peptide (3).

Applicant proposes making two compositions/vaccines by fusing each peptide to an 8 AA linker which is attached to ecdCD40L and expressing those two fusion peptides using plasmid and/or adenoviral vector expression vectors for a VV (prime-boost) or VVV (prime-boost-boost) composition/vaccine or a plasmid composition/vaccine that is administered 2 or 3 times as noted. Neutralizing antibodies to Toxin A have been shown to protect hamsters against a lethal dose of *C difficile*. In addition, the oral administration of a neutralizing antibody to a 3.5 year-old boy from severe *C difficile* infection led to a resolution of the infection (1, 5).

A transcription unit encoding the TAA/ecdCD40L fusion protein will be placed into a plasmid DNA expression vector or an adenoviral expression vector to generate the following two compositions/vaccines: a. pToxinA$_{43,44}$/ecdCD40L, and b. Ad-sig-ToxinA$_{43,44}$/ecdCD40L Unique Structure of Composition/Vaccine against Toxin A: two different but closely related compositions/vaccines are proposed for the induction of neutralizing antibodies to block the binding of Toxin A to its cellular receptor. Each one is comprised of a tandem repeat of 20 amino acids (total size of each antigen=40 AA), each linked to the extracellular domain of CD40L (ecdCD40L) to form a target associated antigen/extracellular domain CD40 ligand (TAA/ecdCD40L). Each of the two tandem repeats are from the region of Toxin A which contacts the cellular receptor which is the necessary first step of the action of Toxins A and B on the cell (1, 3). The sequence of each tandem repeat is unique. This is believed to be the first time that two different tandem repeats from the contact of a ligand with its cellular receptor have been used to prevent binding of the ligand to its cellular receptor.

Joint Mechanism of Action of Toxins A and B: Following the binding of Toxin A and then Toxin B to cellular receptors on colonic mucosal epithelial cells, the toxins are internalized via endocytosis into clathrin coated vesicles. Acidification of the vesicles leads to conformational changes that results in transport of the glucosyltransferase domain (GTD) of the Toxin B across the endosomal membrane. The toxin then undergoes autocleavage (by a cysteine protease domain) leading to release of the glucosyltransferase domain (GTD domain) into the cytosol where it glucosylates and inactivates GTPases such as Rac and Rho leading to cell death (6). Binding of Toxin B to its receptor is mediated by the combined repetitive oligopeptide (CROP) domain at the carboxylterminus (6). Studies have shown that neutralizing antibodies to Toxin B recognize a two tandem repeat sequence in the carboxylterminus of Toxin B.

Composition/Vaccine Against Toxin B: Although neutralizing antibodies to Toxin B, when used alone, are not protective, animal studies have shown that a combination of neutralizing antibodies to both Toxins A and B are more highly protective that when neutralizing antibodies to Toxin A alone are used (1, 7). Thus, we are proposing a TAA/ecdCD40L composition/vaccine against Toxin B to be used in combination with Toxin A.

Deuteration protection experiments (6) with the Toxin B and a neutralizing antibody to Toxin B show that the following peptides/epitopes of Toxin B are protected by the binding of the neutralizing antibody on Toxin B:
  a. AA1902-1914 (AA-EDGFKYFAPNTL) SEQ ID NO. 3
  b. AA2021-2105 (AA-ENGEM) SEQ ID NO. 4
  c. AA2033-2038 (AA-EDGFKY) SEQ ID NO. 5
  d. AA2091-2096 (DEDTAE) SEQ ID NO. 6

A preferred embodiment of Applicant's invention is to combine the several peptides/epitopes SEQ ID NOS 3-6 into one fusion protein for defining a single vaccine as opposed to generating a composition/vaccine for each peptide/epitope.

Thus, we are proposing to use an eight amino acid linker to attach the following 23 aa peptide from Toxin B (which includes the above SEQ ID NOS 3-6) to the amino-terminal end of the ecdCD40L to generate neutralizing antibodies to Toxin B
EDGFKYFAPNTLENGEMDEDTAE SEQ ID NO. 7

This peptide fragment will be attached to ecdCD40L to form the TAA/ecdCD40L fusion protein composition/vaccine in order to induce neutralizing antibodies to Toxin B. Note that as with the composition/vaccine to Toxin A, there are two fragments in Toxin B which are similar (but distinct) which are incorporated into the composition/vaccine by attaching them to the ecdCD40L. In the case of Toxin B composition/vaccine, there are in addition to the two similar (but distinct) peptide fragments, there are, in addition, two unique peptide fragments which are collectively attached in a single linear array before being attached to the ecdCD40L. A transcription unit encoding the fusion protein will be placed into a plasmid DNA expression vector or an adenoviral expression vector to generate the following two compositions/vaccines:

a. pToxinB$_{23AA}$/ecdCD40L
b. Ad-sig-ToxinB$_{23AA}$/ecdCD40L

This will be used alone and in combination with the two toxin A peptide compositions/vaccines and the CDTb composition/vaccine (see below) to determine its effect on protecting mice to a lethal dose of *C difficile*.

Composition/Vaccine Against *Clostridium difficile* transferase (CDT): One of the hallmarks of hypervirulent strains of *C difficile* is the release of a third toxin: an ADP-ribosylating toxin called CDT (4). CDT consists of two components: an enzymatic component (CDTa) and a separate binding component (CDTb). CDTb first interacts with a host receptor on the cell surface. CDTb then undergoes proteolytic activation to form a heptameric prepore on the cell surface (4). The third step is the binding of CDTa to the heptameric CDTb prepore which then is transported with the CDTa to the cellular endosomal compartment via receptor mediated endocytosis. In the acidic environment of the endosome, the prepore then undergoes conformal changes which ultimately are associated with translocation of CDTa into the cytosol. CDTa then catalyzes the ADP-ribosylation of G-actin, at arginine 177 which results in depolymerization of actin and cell death (4).

Truncation studies of CDTb have shown (4) that the region of CDTb that is necessary for binding of CDTb to the cellular receptor (lipolysis-stimulated lipoprotein receptor (LSR)) is defined by a 89 aminoacid region (AA 777-866), near the carboxyl terminal end of CDTb.

The amino acid sequence of this region (4) is as outlined below:

```
                                         SEQ ID NO. 8
AA-779-GNTYINGMYFAPTQTNKEAL DYIQKYRVEATLQYSVRPHS

GFKDIGTKDKMERNYLGDPN QPKTNYVNL

RSYFTGGENIMTYKKLRIYAI-AA869
```

Applicant is proposing to attach the AA779-869 peptide fragment to the amino-terminal of the ecdCD40L by an 8 AA linker. As above, we will create two types of expression vector for the application of this fusion protein composition/vaccine: a plasmid DNA expression vector as well as an adenoviral expression vector which is implemented by sc injection of the Ad-sig-CDTbAA$_{779-869}$/ecdCD40L expression vector or by im injection of the pCDTbAA$_{779-869}$/ecdCD40L plasmid DNA expression vector.

Use of the TAA/ecdCD40L Vaccine Strategy as a *Clostridium difficile* Toxin Transporter Interdiction Strategy: The goal of the TAA/ecdCD40L composition/vaccine strategy is to induce neutralizing antibodies to block and interrupt the process of the cellular uptake of toxins released by *C difficile*. These toxins (the Toxin A/B system as well as the CDTa/CDTb system) are composed of a two-step process the first step of which is the binding of an initial toxin which then facilitates the uptake of a more lethal second toxin.

The first involves the binding of Toxin A which then facilitates the binding and uptake of Toxin B into the intracellular space. The second involves the binding of CDTb which then facilitates the binding and uptake of CDTa into the intracellular space.

This two-step method used in the *Clostridium difficile* toxin transport is a unique method of delivery. The use of a composition/vaccine (TAA/ecdCD40L) for the interdiction of this two-step delivery toxin system to reduce cell death and the death of human subjects is believed to be unique in the area of neutralizing antibodies for protection against the lethal effects of an infectious agent.

Summary of Vaccine Strategy: The proposed composition/vaccine strategy for *C difficile* is to combine and administer at the same time (i) the two compositions/vaccines targeted to induce neutralizing antibodies to the C-terminus of Toxin A (including SEQ ID NOS 1 and 2), (ii) the composition/vaccine designed to induce neutralizing antibodies to the C-terminus of Toxin B (including SEQ ID NO 7), and (iii) the one composition/vaccine designed to induce neutralizing antibodies to CDTb (including SEQ ID NO 8), to determine the effect of mixing these compositions/vaccines on protecting mice from a lethal dose of *C difficile*.

REFERENCES

1. Hussack G, Arbabi-Ghahroudi M, van Faassen H et al. Neutralization of *Clostridium difficile* ToxinA with single-domain antibodies targeting the cell receptor binding domain. Journal of Biological Chemistry 286: 8961-8976, 2011.
2. Ho J G S, Greco A, Rupnik M, and Ng K K S. Crystal structure of receptor-binding C-terminal repeats from *Clostridium difficile* toxin A. PNAS 102: 1837-18378k 2005.
3. Frey S M and Wilkins T D. Localization of two epitopes recognized by monoclonal antibody PCG-4 on *Clostridium difficile* toxin A. Infection and Immunity 60: 2588-2492, 1992.
4. Hemmasi S, Czulkies B A, Schorch B, et al. Interaction of the *Clostridium difficile* binary toxin CDT and its host cell receptor LSR. JBC Papers in Press. Published on Apr. 16, 2015 as Manuscript M115.650523 (http:jbc.org/chi/doi/1011074/jbc.M115.650523)
5. Tjellstrom B, Stenhammar L, Eriksson S and Magnusson K E. Lancet 341: 701-702, 1993.
6. Orth P, Xiao L, Hernandez L D et al. Mechanism of action and epitopes of *Clostridium difficile* toxin B-neutralizing antibody Bezlotoxumab revealed by X-ray crystallography. Journal of Biological Chemistry 289: 18008-18021, 2014.
7. Babcock G J, Broering T J, Hernandez H J et al. Infection and Immunity 74: 6339-6347, 2006.

All references, including publications, patent applications, and patents, cited herein are incorporated by reference in full to the same extent as if each individual publication was specifically and individually indicated to be incorporated by reference. They are indicative of the levels of those of ordinary skill in the art to which the invention pertains and may be employed in the practice of the invention.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed.

Thus, it is understood that the invention is not limited to the disclosed methods, compositions and embodiments shown, including any embodiments that may be apparent to one of ordinary skill in the art. Although the foregoing invention has been described in some detail, it will be readily apparent to those of ordinary skill in the art in light of the teachings of this invention that certain variations and modifications may be made thereto without departing from the spirit or scope of the disclosure herein, including the specific embodiments. Other embodiments are set forth within the following claims.

The invention claimed is:

1. A composition for inducing an immune response against three toxins comprising Toxin A, Toxin B and CDTb, of *Clostridium difficile*, in a subject using four distinct peptide fragments, comprising:

(i) a first peptide fragment from Toxin A, wherein said first peptide fragment is SEQ ID NO. 1, for inducing neutralizing antibodies that bind to Toxin A, (ii) a second peptide fragment from Toxin A, wherein said second peptide fragment is SEQ ID NO. 2, for inducing neutralizing antibodies that bind to Toxin A, (iii) a third peptide fragment from Toxin B, wherein said third peptide fragment is SEQ ID NO. 7, for inducing neutralizing antibodies that bind to Toxin B, and (iv) a fourth peptide fragment of *Clostridium difficile* transferase (CDTb), wherein said fourth peptide fragment is SEQ ID NO. 8, for inducing neutralizing antibodies that bind to the carboxyl terminal region of CDTb, wherein each of said four peptide fragments is connected to an extracellular domain of a CD40L protein (ecdCD40L) to form four separate secretable fusion proteins which combined, form said composition.

2. A composition according to claim 1 wherein a linker is used to attach each of said peptide fragments to the amino terminal of an ecdCD40L.

3. A composition according to claim 1 wherein the four separate secretable fusion proteins are each encoded by a separate viral expression vector for administration to a human subject.

4. A composition according to claim 3 wherein each said viral expression vector is an adenoviral expression vector.

5. A composition according to claim 1 wherein the four separate secretable fusion proteins are each encoded by a plasmid DNA expression vector for administration to a human subject.

6. A method of inducing an immune response against *Clostridium difficile* in a subject comprising administering to said subject an effective amount of the immunogenic composition of claim 1.

* * * * *

SEQUENCE LISTING

```
<160> NUMBER OF SEQ ID NOS: 8

<210> SEQ ID NO 1
<211> LENGTH: 44
<212> TYPE: PRT
<213> ORGANISM: Artificial Sequence
<220> FEATURE:
<223> OTHER INFORMATION: Synthetic Construct

<400> SEQUENCE: 1

Ala Thr Gly Trp Gln Thr Ile Asp Gly Lys Lys Tyr Tyr Phe Asn Thr
1               5                   10                  15

Asn Thr Ala Glu Ala Ala Thr Gly Trp Gln Thr Ile Asp Gly Lys Lys
            20                  25                  30

Tyr Tyr Phe Asn Thr Asn Thr Ala Ile Ala Ser Thr
        35                  40

<210> SEQ ID NO 2
<211> LENGTH: 44
<212> TYPE: PRT
<213> ORGANISM: Artificial Sequence
<220> FEATURE:
<223> OTHER INFORMATION: Synthetic Construct

<400> SEQUENCE: 2

Ala Thr Gly Trp Gln Thr Ile Asp Gly Lys Lys Tyr Tyr Phe Asn Leu
1               5                   10                  15

Asn Thr Ala Glu Ala Ala Thr Gly Trp Gln Thr Ile Asp Gly Lys Lys
            20                  25                  30

Tyr Tyr Phe Asn Thr Asn Thr Phe Ile Ala Ser Thr
        35                  40

<210> SEQ ID NO 3
<211> LENGTH: 12
<212> TYPE: PRT
<213> ORGANISM: Artificial Sequence
<220> FEATURE:
<223> OTHER INFORMATION: Synthetic Construct

<400> SEQUENCE: 3

Glu Asp Gly Phe Lys Tyr Phe Ala Pro Asn Thr Leu
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Synthetic Construct

<400> SEQUENCE: 4

Glu Asn Gly Glu Met
1               5

<210> SEQ ID NO 5
```

```
<211> LENGTH: 6
<212> TYPE: PRT
<213> ORGANISM: Artificial Sequence
<220> FEATURE:
<223> OTHER INFORMATION: Synthetic Construct

<400> SEQUENCE: 5

Glu Asp Gly Phe Lys Tyr
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic Construct

<400> SEQUENCE: 6

Asp Glu Asp Thr Ala Glu
1               5

<210> SEQ ID NO 7
<211> LENGTH: 23
<212> TYPE: PRT
<213> ORGANISM: Artificial Sequence
<220> FEATURE:
<223> OTHER INFORMATION: Synthetic Construct

<400> SEQUENCE: 7

Glu Asp Gly Phe Lys Tyr Phe Ala Pro Asn Thr Leu Glu Asn Gly Glu
1               5                   10                  15

Met Asp Glu Asp Thr Ala Glu
            20

<210> SEQ ID NO 8
<211> LENGTH: 90
<212> TYPE: PRT
<213> ORGANISM: Artificial Sequence
<220> FEATURE:
<223> OTHER INFORMATION: Synthetic Construct

<400> SEQUENCE: 8

Gly Asn Thr Tyr Ile Asn Gly Met Tyr Phe Ala Pro Thr Gln Thr Asn
1               5                   10                  15

Lys Glu Ala Leu Asp Tyr Ile Gln Lys Tyr Arg Val Glu Ala Thr Leu
            20                  25                  30

Gln Tyr Ser Val Arg Pro His Ser Gly Phe Lys Asp Ile Gly Thr Lys
        35                  40                  45

Asp Lys Met Glu Arg Asn Tyr Leu Gly Asp Pro Asn Gln Pro Lys Thr
    50                  55                  60

Asn Tyr Val Asn Leu Arg Ser Tyr Phe Thr Gly Gly Glu Asn Ile Met
65                  70                  75                  80

Thr Tyr Lys Lys Leu Arg Ile Tyr Ala Ile
                85                  90
```